(12) United States Patent
Sackeim

(10) Patent No.: US 10,583,288 B2
(45) Date of Patent: *Mar. 10, 2020

(54) THERAPY DEVICE WITH CURRENT ADJUSTMENT

(71) Applicant: Mecta Corporation, Tualatin, OR (US)

(72) Inventor: Harold A. Sackeim, Fleetwood, PA (US)

(73) Assignee: MECTA CORPORATION, Tualatin, OR (US)

(*) Notice: Subject to any disclaimer, the term of this patent is extended or adjusted under 35 U.S.C. 154(b) by 0 days.

This patent is subject to a terminal disclaimer.

(21) Appl. No.: 15/696,872

(22) Filed: Sep. 6, 2017

(65) Prior Publication Data

US 2018/0056064 A1    Mar. 1, 2018

Related U.S. Application Data

(60) Continuation of application No. 14/262,234, filed on Apr. 25, 2014, now Pat. No. 9,789,310, which is a division of application No. 12/464,545, filed on May 12, 2009, now Pat. No. 8,712,532.

(51) Int. Cl.
*A61N 1/36* (2006.01)
*A61N 1/38* (2006.01)
*A61N 1/372* (2006.01)

(52) U.S. Cl.
CPC ..... *A61N 1/36014* (2013.01); *A61N 1/36025* (2013.01); *A61N 1/3727* (2013.01); *A61N 1/38* (2013.01)

(58) Field of Classification Search
CPC ............ A61N 1/36014; A61N 1/36025; A61N 1/3727; A61N 1/38
See application file for complete search history.

(56) References Cited

U.S. PATENT DOCUMENTS

| | | | |
|---|---|---|---|
| 4,305,402 A * | 12/1981 | Katims | A61B 5/0484 128/905 |
| 5,755,744 A | 5/1998 | Shaw et al. | |
| 5,871,517 A | 2/1999 | Abrams et al. | |
| 6,014,587 A | 1/2000 | Shaw et al. | |

(Continued)

OTHER PUBLICATIONS

Sackeim, "Convulsant and Anticonvulsant Properties of Electroconvulsive Therapy: Towards a Focal Form Brain Stimulation", Clinical Neuroscience Research, 2004, pp. 39-57, Elsevier B.V.

(Continued)

*Primary Examiner* — Allen Porter
*Assistant Examiner* — Natasha Patel
(74) *Attorney, Agent, or Firm* — Miller Nash Graham & Dunn LLP

(57) ABSTRACT

An ECT system capable of focusing the electrical signals on a specific portion of the patient's brain is provided. The ECT system includes a means of applying unidirectional electrical signals and asymmetric electrodes for focusing the signals on the patient. A method of titrating an electroconvulsive therapy (ECT) system and a method of operating an ECT system are also provided. The method includes setting an initial current value, administering an ECT signal to the patient, determining if the seizure threshold has been achieved, and repeating as necessary until the seizure threshold is achieved.

8 Claims, 7 Drawing Sheets

(56) References Cited

U.S. PATENT DOCUMENTS

| | | |
|---|---|---|
| 2005/0165458 A1 | 7/2005 | Boveja et al. |
| 2006/0173510 A1* | 8/2006 | Besio .................. A61B 5/0482 607/45 |
| 2007/0156182 A1 | 7/2007 | Castel et al. |
| 2007/0265664 A1 | 11/2007 | Gerber et al. |
| 2008/0188905 A1* | 8/2008 | Swartz ............... A61N 1/36025 607/45 |
| 2008/0294209 A1 | 11/2008 | Thompson et al. |
| 2012/0209346 A1 | 8/2012 | Bikson et al. |

OTHER PUBLICATIONS

Spellman, et al., "Focal Electrically Administered Seizure Therapy: A Novel form of ECT Illustrates the Roles of Current Directionality, Polarity, and Electrode Configuration in Seizure Induction," Neuropsychopharmacology (2009), pp. 1-9.

* cited by examiner

THERAPY DEVICE WITH CURRENT ADJUSTMENT

CROSS REFERENCE TO RELATED APPLICATIONS

This application is a continuation of and claims priority to U.S. patent application Ser. No. 14/262,234, entitled APPARATUS AND METHOD FOR ELECTRICALLY ADMINISTERED SEIZURE THERAPY USING TITRATION IN THE CURRENT DOMAIN, filed Apr. 25, 2014, which is a division of U.S. patent application Ser. No. 12/464,545, entitled METHOD AND APPARATUS FOR FOCUSING ELECTRICAL STIMULATION IN THE BRAIN DURING ELECTRO-CONVULSIVE THERAPY, which issued on Apr. 29, 2014, as U.S. Pat. No. 8,712,532, the contents both of which are incorporated by reference herein.

BACKGROUND

Technical Field

The invention relates generally to the field of electroconvulsive therapy. Specifically, the invention relates to a system and method of administering focused electro-convulsive therapy using titration in the current domain.

Description of the Related Art

Seizure therapy was first recognized as a viable treatment for Schizophrenia in 1934 by the Hungarian neuropsychiatrist Von Meduna. Early seizure therapies used pharmacological inducement methods. These early pharmacological methods were plagued by adverse side effects unpredictability. In 1937, two Italian physicians, Cerletti and Bini, used electrical stimulation to induce the seizures for the seizure therapy. The success of this method quickly led to its adoption throughout the world. The use of electrical stimulation to induce seizures is generally referred to as electroconvulsive therapy (ECT).

ECT was in widespread use in the 1940's and 1950's for treatment of many severe mental health disorders including schizophrenia. However, the development of pharmacological alternatives to seizure therapy in the mid-1950's signaled the decline of ECT use. Currently, ECT is only sparingly used. However, due to limitations in the pharmacological alternatives, many psychiatrists have recognized the continuing viability of ECT and some have suggested that ECT use may be increasing.

Early ECT systems used standard 50 or 60 Hz sine wave electrical signals as this type of signal was readily available on the consumer power grid. Once researchers had established a set of stimulus parameters that was effective at producing seizures, there was no longer a need for ECT systems to have parameter varying controls. Consequently, some early ECT systems were not much more than a wall outlet plug, a voltage or current knob, and an ON/OFF switch.

Eventually, the electrically induced signals were associated with adverse side effects in the patients such as confusion and amnesia. This led researchers to experiment with the stimulus signals to try to reduce or eliminate the side effects of the treatment. This research led to ECT devices capable of providing a pulse waveform stimulus. Further, prominent ECT researcher, Paul Blachley, decided that, an optimal ECT device should incorporate the capability of monitoring both electroencephalograph (EEG) and electrocardiogram (ECG) signals, have the ability to test the safety of the electrical circuit before delivering the stimulus, and have the ability to allow careful titration to individuals' seizure thresholds. After design and testing efforts, the device envisioned by Blachley, which was known as the MECTA (Monitored Electro-Convulsive Therapy Apparatus) went on the market in 1973, and readily grew in popularity over the following years. Additional improvements continued to be made to the MECTA system over the years including safety improvements and the capability of continuous signal monitoring during treatment.

Conventional ECT systems use alternating current (ac) signals. Typically, when using ac signals to generate seizures, symmetric electrodes are used on the patient. Since the electrodes are symmetric and the current is bidirectional, the current distribution in the patient will be essentially symmetric in the vicinity of both electrodes. Consequently, with conventional ECT systems, the ability to focus the electrical signals on a specific portion of the patient's brain is extremely limited.

Also, in administering ECT, it is important to calibrate the ECT system to the individual patient's seizure threshold. This process is called titration. The titration process is important to ensure that seizures are generated in the most efficient way possible. Efficiently generating the seizures allows for more effective treatment and minimizes the side effects of the treatment to the patient. Conventional ECT systems use a total charge energy titration method in which the pulse width or number of pulses of the signals is manipulated until the patient's seizure threshold is reached. Unfortunately, it is not possible in conventional systems to perform the titration process by varying only the current. However, the ability to perform a titration process by only adjusting the current, may lead to more efficient determination of the patient's seizure threshold and minimize adverse side effects to the patient.

The invention addresses these and other disadvantages of the conventional art.

SUMMARY

The disclosure provides an ECT system with the capability of focusing the electrical signals on a specific portion of the patient's brain. The system includes a means of applying unidirectional electrical signals and asymmetric electrodes for focusing the signals on the patient. The disclosure also provides a method of operating an ECT system including titration in the current domain. Using the titration method of the invention allows a more precise determination of the seizure threshold and thereby, minimizes adverse side effects of the ECT treatment on the patient.

BRIEF DESCRIPTION OF THE DRAWINGS

The above and other objects, features and advantages of the disclosure will be more clearly understood from the following detailed description taken in conjunction with the accompanying drawings, in which:

FIGS. 3A through 6A are cross-sectional views of negative electrodes according to some embodiments of the invention;

FIGS. 3B through 6B are plan views of negative electrodes according to some embodiments of the invention;

DETAILED DESCRIPTION OF PREFERRED EMBODIMENTS

Figure 1:
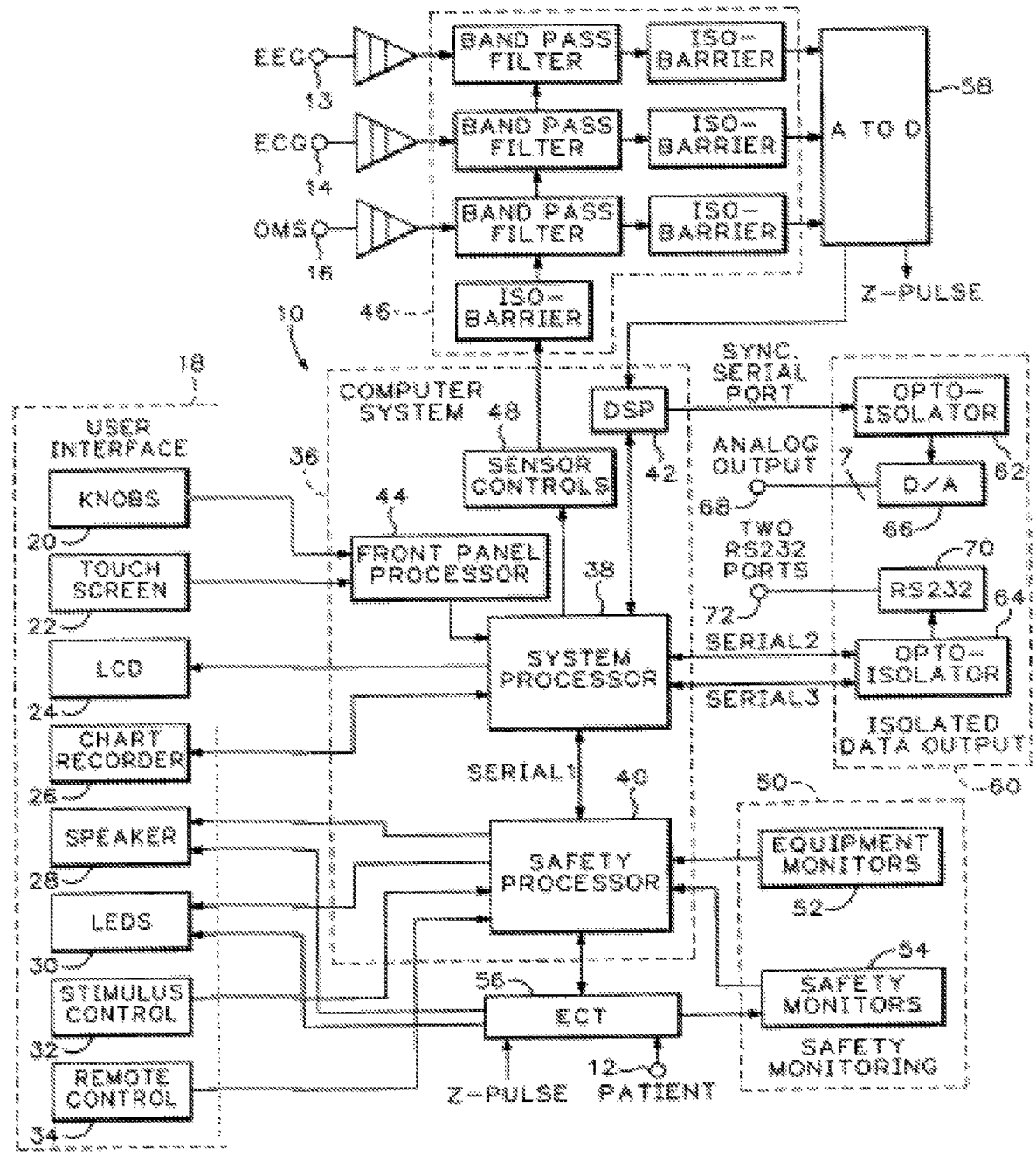
FIG. 1 is a block diagram of an ECT system according to the invention.

Example embodiments are described below with reference to the accompanying drawings. Many different forms and embodiments are possible without deviating from the spirit and teachings of this disclosure and so the disclosure should not be construed as limited to the example embodiments set forth herein. Rather, these example embodiments are provided so that this disclosure will be thorough and complete, and will fully convey the scope of the disclosure to those skilled in the art. In the drawings, the sizes and relative sizes of components and regions may be exaggerated for clarity.

It will be understood that, although the terms first, second, third, etc. may be used herein to describe various elements, components, regions, layers and/or sections, these elements, components, regions, layers and/or sections should not be limited by these terms. These terms are only used to distinguish one element, component, region, layer or section from another element, region, layer or section. Thus, a first element, component, region, layer or section discussed below could be termed a second element, component, region, layer or section without departing from the teachings of the disclosure.

The terminology used herein is for the purpose of describing particular example embodiments only and is not intended to be limiting. As used herein, the singular forms "a," "an" and "the" are intended to include the plural forms as well, unless the context clearly indicates otherwise. It will be further understood that the terms "comprises" and/or "comprising," when used in this specification, specify the presence of stated features, elements, and/or components, but do not preclude the presence or addition of one or more other features, elements, components, and/or groups thereof.

Unless otherwise defined, all terms (including technical and scientific terms) used herein have the same meaning as commonly understood by one skilled in the art to which this disclosure pertains. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

FIG. 1 is a block diagram of an ECT system according to the invention.

Referring to FIG. 1, an ECT system 10 includes several connections to the patient. The first connection is the ECT stimulus electrodes 12 through which an ECT treatment signal is applied to the patient. The ECT system 10 also includes several patient monitoring inputs 13, 14 and 16 that connect to the patient to receive EEG, ECG and/or OMS (optical motion sensor) signals, respectively.

The ECT system 10 further includes a user interface 18 through which the user, typically a psychiatrist, interacts or interfaces with the ECT system 10. In one embodiment of the user interface, a plurality of knobs 20 is included for setting the parameters that define the ECT signals. These parameters include the frequency of the signal, the pulse width of each individual pulse in the signal, the current level, and the duration of the ECT signal. According to some embodiments, the current of the ECT signal can be adjusted independent of the voltage using the knobs 20 on the user interface 18. The current may also be adjusted independently using the other input means described below, such as the touch screen 22.

The user interface 18 also includes a touch screen 22 which is a touch-sensitive display that allows the user to input commands to the system by touching certain portions of the screen. The system is menu driven so that the user can quickly and efficiently move through the command options. A display 24 is provided to display certain information to the user both prior to and during treatment. A chart recorder 26 provides a hard copy output of the patient monitoring signals. The ECT system 10 further includes a speaker 28 that sounds an audible alarm when certain failures occur in the system and as a safety feature whenever the ECT section is activated. Indicators 30 are also provided as indicator lights for the user. A stimulus control section 32 is provided to allow the user to initiate a treatment. A remote control section 34 may also be provided that allows the user to initiate a treatment while out of reach of the stimulus control section 32. The remote control section 34, which works in conjunction with the paddles (334B, 336B of FIG. 2B), disables the (front panel) stimulus control section 32 so that when remote-control-equipped paddles are plugged into the ECT system 10, a treatment cannot accidentally be initiated from the stimulus control section 32 on the user interface 18.

At the heart of the ECT system 10 is a computer system 36 which orchestrates the operation of the system. The computer system includes four processors: a system processor 38, a safety processor 40, a digital signal processor 42, and a front panel processor 44. The system processor 38 is coupled to the knobs 20, the touch screen 22, the display 24, and the chart recorder 26 of the user interface 18. The knobs 20 and touch screen 22 are coupled to the system processor 38 via the front panel processor 44 that emulates a standard keyboard interface. Thus, the system processor communicates to and from the knobs 20 and the touch screen 22 as it would communicate with a standard IBM keyboard. Thus, the knobs 20 and the touch screen 22 can be replaced by a keyboard to provide input to the ECT system 10 for testing and maintenance.

The system processor 38 is also coupled to a patient monitoring section 46 through a sensor control block 48. The sensor control block 48 includes logic that decodes signals received from the system processor 38 and configures the patient monitoring section 46 into various modes responsive thereto. These modes include the normal operational mode in which the patient monitoring signals are received from the patient and test modes wherein the accuracy of the section is tested.

The computer system 36 also includes a safety processor 40. The safety processor 40 is primarily responsible for creating and controlling delivery of the stimulus waveform and coordinating the various safety tests and checks that are performed on and by the ECT system 10. The safety processor 40 is coupled to the system processor 38 via a serial interface (SERIAL 1). The safety processor 40 is also coupled to a safety monitoring section 50 which includes equipment monitors 52 and safety monitors 54. These monitors 52 and 54 monitor both the equipment as well as the stimulus to determine whether or not the system is performing within specification and, if not, to disable any further treatments.

The safety monitor 54 is further coupled to an ECT block 56 which generates the ECT signal responsive to the safety processor 40. The ECT block 56 is directly coupled to the timing circuits of an A-to-D converter 58 to receive a Z_PULSE signal that is generated during every sample taken by the A-to-D converter 58. The Z_PULSE signal is used by the impedance-measuring portion of the ECT block 56 to measure patient impedance. The A-to-D converter 58 digitizes the patient monitoring signals received at inputs 13, 14 and 16 (i.e., EEG, ECG and OMS). This digitized data is then operated on by the DSP 42 to filter out unwanted power line frequency interference by the use of a frequency adaptive finite impulse response (FIR) filter as well as to decimate the digitized data for display.

Safety processor 40 is directly coupled to the speaker 28, the indicators 30, the stimulus control 32, and the remote control 34. The safety processor 40 initiates an ECT treatment sequence, under certain predetermined conditions, responsive to inputs received from either the stimulus control 32 or the remote control 34. Both the ECT block 56 and the safety processor 40 also actuate either the speaker 28 or the indicators 30 if certain conditions exist, e.g., internal self-test failed. This provides redundant fault and "arming status" indications for safety purposes.

The final section of the ECT system 10 is the isolated data output section 60. This section is coupled to the computer system 36 via three serial ports: a synchronous serial port (SYNC SERIAL PORT) and two asynchronous serial ports (SERIAL 2, SERIAL 3). The computer system 36 is isolated from the isolated data output section 60 by opto-isolator blocks 62 and 64. The opto-isolator block 62 is interposed between the DSP 42 and a digital-to-analog converter 66. The DSP 42 transmits the digitized patient monitoring signals to the digital-to-analog converter 66 in order that those signals may be observed by external equipment coupled to analog outputs 68. Similarly, the system processor 38 communicates the display data via opto-isolator block 64 to an RS-232 interface block 70, which provides two RS-232 serial output ports 72 to enable this data to be stored, displayed, or printed by an external computer. The opto-isolators, 62 and 64, here protect the patient and the operator from shock hazards that may occur due to, e.g., electrical faults.

The construction and operation of the ECT system 10 is described in greater detail in U.S. Pat. Nos. 5,755,744 and 6,014,587, which are herein incorporated by reference in their entirety.

Figure 2A:
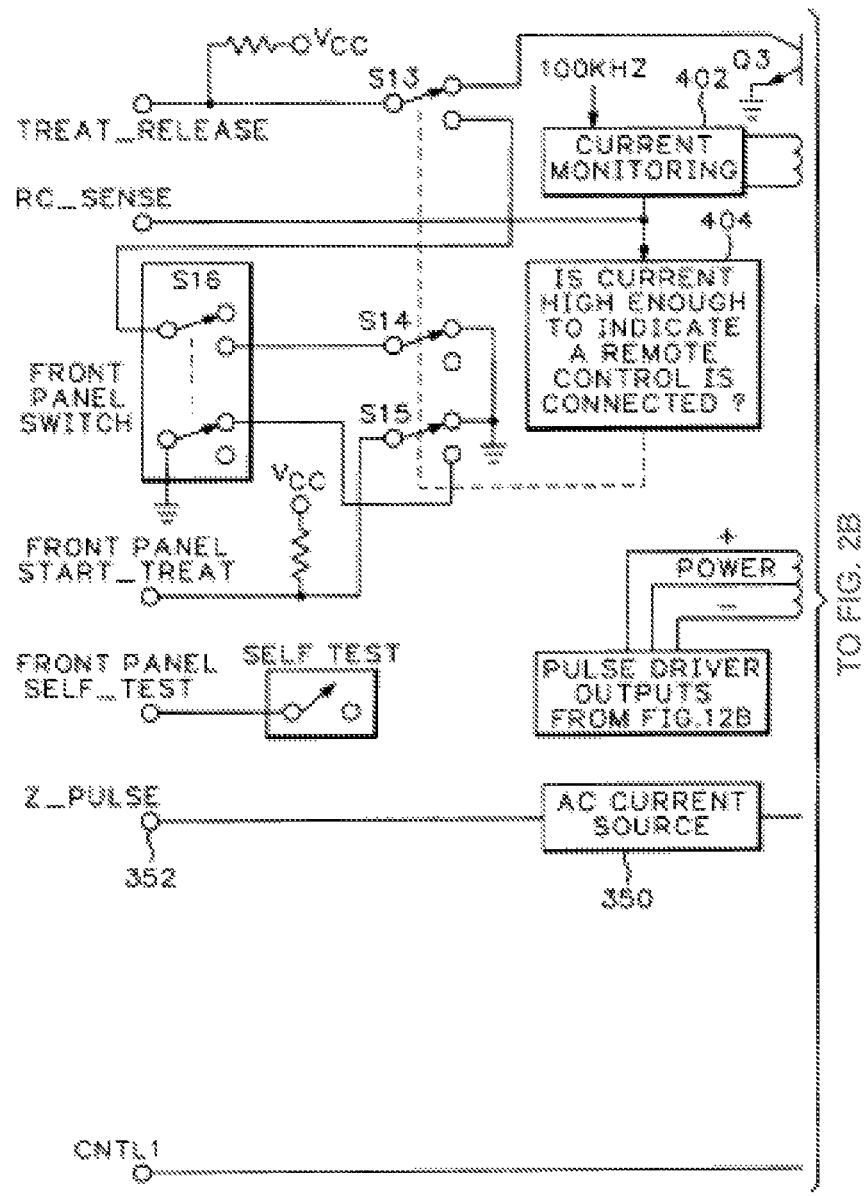
FIGS. 2A and 2B are block diagrams of the delivery circuitry and hardware safety monitors of the system shown in FIG. 1.
Figure 2B:
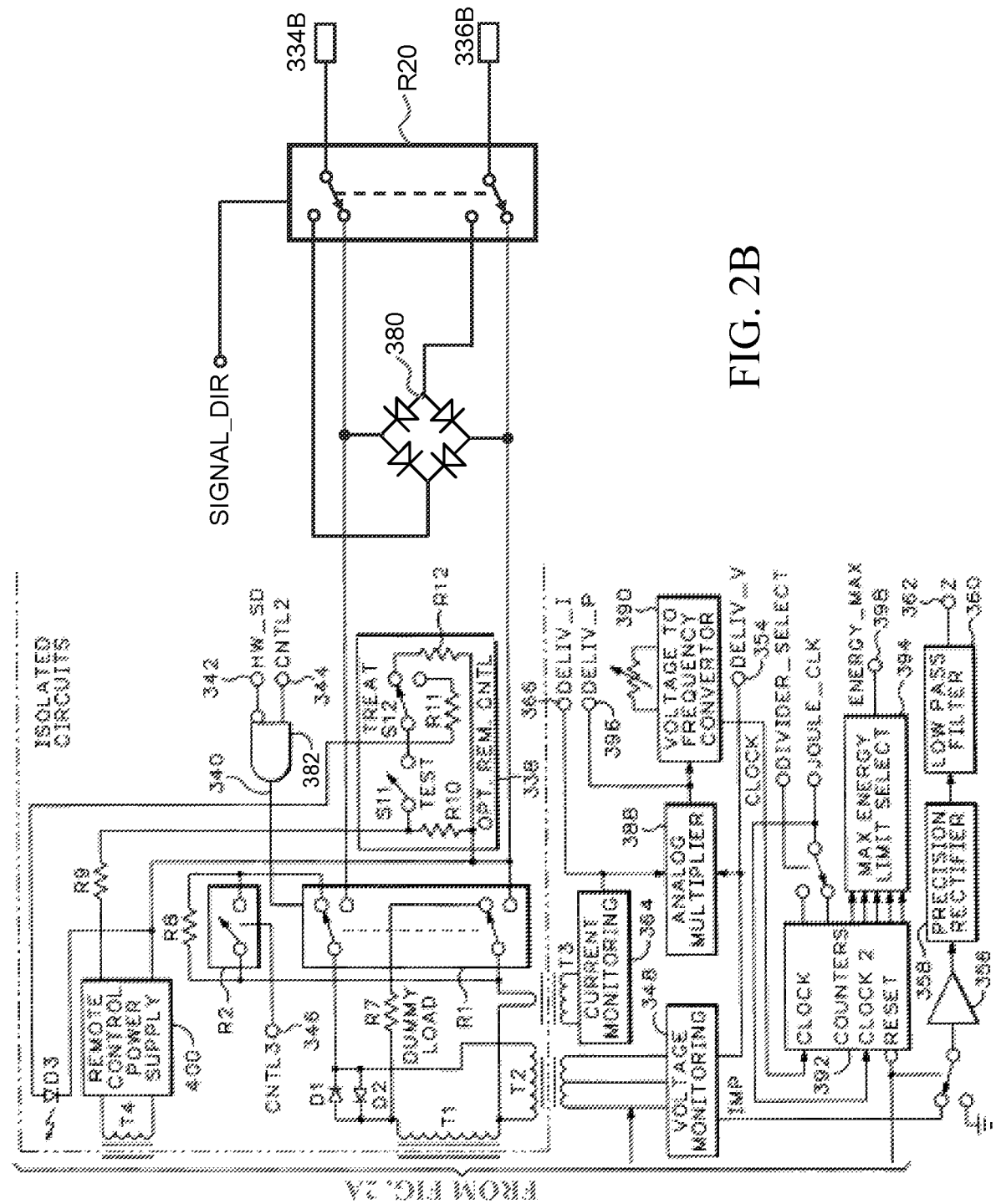

FIGS. 2A and 2B are block diagrams of the delivery circuitry and hardware of the safety monitors of the system shown in FIG. 1.

Referring to FIGS. 2A and 2B, the three outputs of a pulse driver (+, −, and POWER) are connected to the center-tapped primary winding of a first transformer T1. The first transformer T1 is a step up transformer so that the voltage across the secondary winding is equal to the turns ratio times the voltage across the primary. The current in the secondary, on the other hand, is reduced by the turns ratio. In the preferred embodiment, the turns ratio is equal to 16.6:1.

A relay R1 is interposed between the outputs of the secondary winding and the two paddles 334B and 336B. The optional remote control unit 338 is shown connected between relay R1 and the paddles 334B and 336B. However, the optional remote control unit 338 is not required. When the optional remote control unit 338 is not provided, paddles 334B and 336B could be simple electrodes that are used when the treatment is initiated from the stimulus control section 32.

The relay R1 is used to switch a dummy load R7 into and out of the circuit of the secondary winding of the first transformer T1. When the relay is in the position shown in FIG. 2B, the dummy load R7 is switched into the circuit and when the relay R1 is in its other position, the dummy load R7 is taken out of the circuit and the winding is connected to the paddles 334B and 336B. The state of the relay R1 is controlled by a logic gate 382 whose output is connected to the coil of the relay via line 340. The logic gate 382 includes two inputs 342 and 344 for receiving a hardware shutdown signal HW_SD and a control signal CNTL2. The logic gate 382 switches from the dummy load to the patient, i.e., the paddles, if the control signal CNTL2 is asserted and the hardware shutdown signal HW_SD is not asserted. This provides the system with the ability to shunt the pulse to the dummy load R7 under software control as indicated by the assertion of the control signal CNTL2, which is under control of the safety processor 40. The control signal CNTL2 allows the system to perform an internal self-test in which a pre-treatment ECT signal is applied to the dummy load R7 and the characteristics of the ECT signal are then examined by the safety hardware and the system rendered inoperable if any of these safety tests fail.

The safety monitoring section also includes a second relay R2, which is used to either short out, or leave unshunted, a 5 Kohm resistor R8 in the output circuit under certain test conditions. This 5 Kohm load is shorted by R2, thus effectively shorting the secondary winding of the first transformer T1 when a control signal CNTL3 is asserted. This control signal is applied to the coil of relay R2 via input 346. The 5 Kohm resistor and relay R2 are used during the self-tests of the instrument's ability to measure static impedances at zero ohms and 5 Kohms.

A second transformer T2 is used to measure the voltage delivered to the dummy load during pre-treatment testing. The voltage across the primary of the second transformer T2 is stepped down to the secondary, which is then measured by a voltage monitoring circuit 348. A current is provided to the secondary winding by an AC current source 350, which generates a fixed current responsive to the Z_PULSE received on input 352. This causes a current of approximately 40 µA through the secondary of the second transformer T2. Because the current AC amplitude is fixed, then the voltage measured by the voltage monitoring circuit 348 is proportional to the static impedance (of the patient or of the impedance self-test resistor R8). The measured voltage DELIV_V is provided to the safety processor 40 from the voltage monitoring circuit 348 on output 354. A signal corresponding to the measured impedance IMP is provided by the voltage monitoring circuit 348 to an amplifier 356 whose output is then rectified by precision rectifier 358 and filtered by low pass filter 360. The output of low pass filter 360 is a signal Z on output 362 that is proportional to the measured static impedance.

The circuits described above measure what is termed "static" impedance. Static impedance in the context of ECT is the impedance measured under test conditions of very low currents applied to the patient (or test resistors). Static impedance changes little with continued application of the current used to perform the measurement. "Dynamic" impedance in the context of ECT, on the other hand, is the effective impedance presented by the patient's scalp and the paddle electrodes to the applied treatment current. Dynamic impedance is the impedance observed at very high applied currents, where the scalp tissue exhibits non-linear impedance behavior. The dynamic impedance seen in ECT is much lower than the static impedance seen in ECT, and furthermore, decreases generally during the duration of the treatment. Dynamic impedance is calculated by the system processor by dividing the delivered voltage by the delivered current. Signal Z on line 362 is not used to obtain dynamic impedance.

The circuit also includes a third transformer T3, which is used to measure the current through the output circuit of the first transformer T1. The third transformer T3 is a (voltage) step up transformer whose secondary is coupled to a current monitoring circuit 364 which measures the current through the output circuit. This measured current signal DELIV_I is then provided to the safety processor 40 on output 366.

The circuit also provides an energy monitor circuit. The energy monitor includes an analog multiplier 388, a voltage-to-frequency converter 390, a two-stage counter 392 and an energy limit select circuit 394. The analog multiplier has two inputs: one of which is connected to the voltage monitoring circuit 348 to receive the measured voltage signal DELIV_V; and the second input is connected to the current monitoring circuit 364 to receive the measured current signal DELIV_I. The analog multiplier then multiplies these two signals together to produce a delivered power signal DELIV_P on output 396. The delivered power signal is then provided to a voltage-to-frequency converter 390 which converts the voltage level of the delivered power signal to a clock signal having a frequency proportional to that power signal level. The clock signal is provided to a clock input of a counter 392, which, in the preferred embodiment, is implemented by cascading two binary counters. The counters produce a binary count that increments with each rising edge of the clock signal from the voltage-to-frequency converter 390. This binary count is then provided to a maximum energy limit select circuit 394 which compares the binary count to a preset limit. If the binary count exceeds this preset limit, the circuit 394 asserts a signal ENERGY_MAX on output 398 to indicate that the amount of energy delivered to the patient during this treatment has exceeded a pre-selected limit. In the preferred embodiment, the pre-selected limit is adjustable with the use of jumpers to allow for different limits to be set in different countries or under different conditions. It should be apparent that the voltage-to-frequency converter 390 and counter 392 are but one implementation of what is essentially an integrator, which integrates the delivered power signal DELIV_P over time. Other integrators, of course, can be used.

The paddles 334B and 336B may be part of an optional remote control package that allows the user to initiate an ECT treatment from the paddles 334B and 336B. Otherwise, the user can only initiate a treatment from the front panel 'Start Treatment' switch. One of the paddles includes a two-stage switch represented by switches S11 and S12 in FIG. 2B. The first switch S11 initiates a pre-treatment test sequence. Actuation of the first switch S11 is detected by measuring the current through the optional remote control unit. This is accomplished by switching different resistances into the circuit according to which switch is actuated. The first switch S11 is normally open, as indicated in FIG. 2B. In addition, the second switch S12 is normally in the position shown. In this default state, a circuit is formed with resistors R9 and R10 across which a voltage is supplied by remote control power supply 400. The current supplied by the power supply 400 is detected by a current monitoring circuit 402 which is coupled to the power supply 400 by a fourth transformer T4. The current monitor 402 produces a signal RC_SENSE, which is proportional to the measured current supplied by the power supply 400. This signal RC_SENSE is provided to a threshold detector 404, which compares the current level of the signal RC_SENSE to determine whether the current level exceeds a predetermined amount. If insufficient current is detected, the circuit 404 assumes that the remote control unit 338 is not connected. If the circuit, however, detects this minimum current level, then the circuit 404 switches the state of switches S13, S14 and S15 so as to disable the front panel switch S16 so that a treatment cannot accidentally be initiated from the stimulus control section 32 on the user interface 18.

If the test switch S11 is actuated, on the other hand, resistor R12 is coupled in parallel with resistor R10, thereby presenting a different load to the remote control power supply 400. This current is also measured by the current monitor 402.

The treatment switch S12 actually corresponds to the second stage of the two-stage switch comprised of S11 and S12. Therefore, S12 can only be actuated if S11 is also actuated. If S12 is actuated (and therefore S11), a circuit is formed with R9, R11 and light-emitting diode D3 of an opto-coupler. Passing a current through diode D3 causes a signal to be produced by optical detector Q3, which is then passed on to the safety processor as the TREATS_RELEASE signal through switch S13. This signal can then be used to determine if the treatment switch S12 is released prior to the full treatment duration that was programmed by the front panel controls.

A bridge rectifier 380 may be interposed between the relay R1 and the paddles 334B and 336B depending on the position of a relay R20. The position of the relay R20 is determined by the signal SIGNAL_DIR. When the relay R20 is in the position shown in FIG. 2B (the first position), a bi-directional, or pulsed alternating current, signal is applied directly from the relay R1 to the paddles 334B and 336B. In other words, when the relay R20 is in the first position, the bridge rectifier 380 is bypassed. However, when the relay R20 is in the second position (the opposite position of that shown in FIG. 11B), the relay R1 is coupled to the paddles 334B and 336B through the bridge rectifier 380, thereby delivering a unidirectional, or pulsed direct current, ECT signal to the paddles 334B and 336B. When the unidirectional ECT signal is applied to the paddles 334B and 336B, the paddle 334B can be referred to as a positive paddle and the paddle 336B can be referred to as a negative paddle. Due to the varying response of the brain to the direction of the current, the unidirectional ECT signal can be used to focus the ECT stimulus on specific portions of the patient's brain, thereby providing more efficient treatment.

FIGS. 3A through 6A are cross-sectional views of negative electrodes according to some embodiments of the invention. FIGS. 3B through 6B are plan views of negative electrodes according to some embodiments of the invention.

In conventional ECT systems, the electrodes attached to the paddles 334B and 336B are symmetric. In other words, the electrodes attached to the paddles 334B and 336B are the same for both paddles. The electrodes in conventional systems are typically circular with a diameter of about 2 inches. However, according to the invention, the electrodes attached to the paddles 334B and 336B are asymmetric. In other words, the electrode attached to the positive paddle 334B (the positive electrode) may be different in one or more of size, shape, and area from the electrode attached to the negative paddle 336B (the negative electrode). According to some embodiments, both the positive and negative electrodes are made from solid 303 stainless steel. However, the positive and negative electrodes may be made from different materials. Also, the positive electrode may be made from a different material than the negative electrode.

Figure 5A:
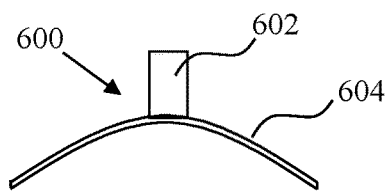
Figure 5B:
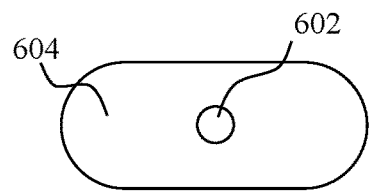
Figure 6A:
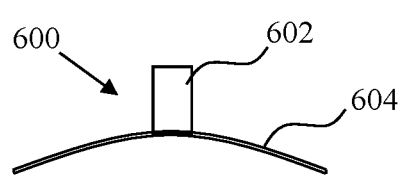
Figure 6B:
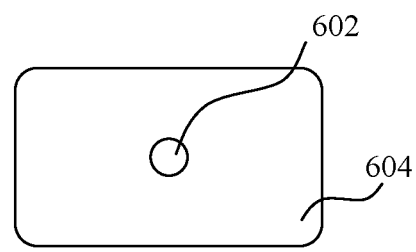
Figure 7A:
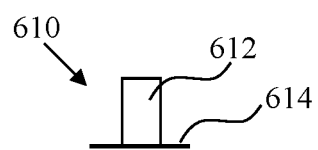
FIG. 7A is a cross-sectional view of a positive electrode according to an embodiment of the invention.
Figure 7B:
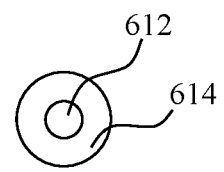
FIG. 7B is a plan view of a positive electrode according to an embodiment of the invention.

Referring to FIGS. 3A through 6B, a negative electrode 600 includes an electrical contact portion 602 and a patient contact portion 604. The electrical contact portion 602 electrically connects the negative electrode 600 to the negative paddle 336B. The patient contact portion 604 of the negative electrode 600 is placed on the patient's scalp during treatment along with the positive electrode 610 (as shown in FIGS. 7A and 7B) and determines the distribution of the electrical current in the patient's brain. The electrical contact portion 602 may be generally cylindrical in shape. According to some embodiments, the electrical contact portion 602 is cylindrically shaped and has a height of about 0.5 inches and a diameter of about 0.32 inches.

Figure 3A:
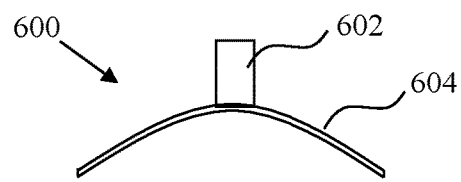
Figure 3B:
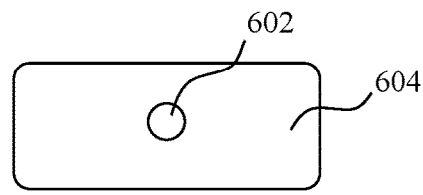
Figure 4A:
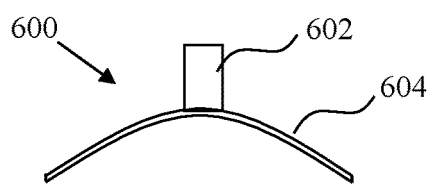
Figure 4B:
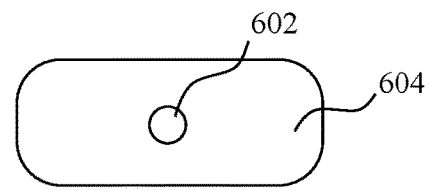

The patient contact portion 604 may be substantially rectangular in shape, with rounded corners. According to some embodiments, the patient contact portion 604 may be rectangular with the length of the short axis of about 1 inch and the length of the long axis of about 2.5 inches. The corners may have a small radius of curvature as shown in FIG. 3B or a greater radius of curvature as shown in FIG. 4B. As an example, the radius of curvature of the patient contact portion 604 in FIGS. 3B and 4B may be about 0.125 and 0.25 inches, respectively. The corners may have an even greater radius of curvature as shown in FIG. 5B, such that the sides of the patient contact portion 604 are substantially semicircular. As an example, the radius of curvature of the patient contact portion 604 in FIG. 5B may be about 0.5 inches. According to a preferred embodiment, as shown in FIGS. 6A and 6B, the patient contact portion 604 may be substantially rectangular with short and long axis lengths of 2 and 3 inches, respectively, with a radius of curvature of the corners of 0.25 inches.

FIG. 7A is a cross-sectional view of a positive electrode according to an embodiment of the invention. FIG. 7B is a plan view of a positive electrode according to an embodiment of the invention.

Referring to FIGS. 7A and 7B, the positive electrode 610 may include an electrical contact portion 612 and a patient contact portion 614. The electrical contact portion 612 of the positive electrode 610 may be substantially similar to the electrical contact portion 602 of the negative electrode 600 described above. The patient contact portion 614 of the positive electrode 610 may be substantially different in one or more of size, shape, and area from the patient contact portion 604 of the negative electrode 600. For example, the patient contact portion 614 of the positive electrode 610 may be substantially circular shaped with a diameter of about 0.75 inches.

Figure 8:
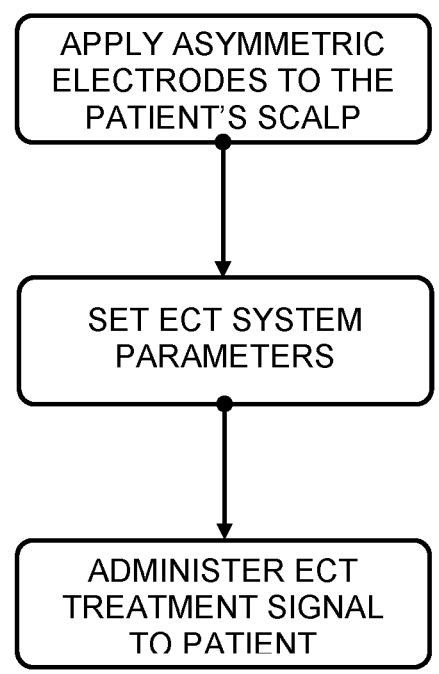
FIG. 8 is a flowchart of a method of providing Focal Electrically Administered Seizure Therapy to a patient.

FIG. 8 is a flowchart of a method of providing Focal Electrically Administered Seizure Therapy to a patient.

Referring to FIG. 8, the first step in the method of providing ECT to a patient consists of applying electrodes to the patient's scalp. When asymmetric electrodes are used, the electrodes may be arranged on the patient's scalp so as to focus electrical signals on a specific portion of the patient's brain. As an example, a negative electrode may be positioned on a posterior portion of the patient's head and the positive electrode may be positioned on an anterior portion of the head. Further, the negative electrode may be larger than the positive electrode. Next, a titration procedure is performed on the patient. The titration procedure is used to estimate the seizure threshold, or the lowest dose of electricity needed to produce a seizure. Titration usually is conducted at the first treatment of a patient with an electrical stimulus administration that is sufficiently low so that most patients do not have a seizure. As an example, the first electrical stimulus may be at a level at which a seizure would result in only about 15% of the general population. If in fact no seizure occurs, one or more parameters of the ECT signal are changed and the modified stimulus is applied to the patient. This process of applying the signal, determining if a seizure results, and adjusting the ECT signal is repeated until a satisfactory seizure is produced. Generally, the titration procedure must be completed within five applications of the stimulus to the patient in a single session due to limitations on the patient's physiology and the capabilities of anesthetic technology.

A titration procedure is desirable before administering ECT treatment because there are marked individual differences among patients in their seizure threshold. Using standard approaches to titration, at least a 50-fold range has been identified in seizure threshold values. A good deal of this variability is due to individual differences in skull anatomy resulting in variability of current shunted away from the brain through the scalp and skull. Only a small portion of current in any pulse actually enters the brain. In the past, titrating dosage has been primarily manipulated in terms of the number of pulses; either by manipulating the frequency of pulses (i.e. the number of pulses per second) or the duration of the pulse train. Despite the fact that people vary in the amplitude of the pulse in their brain tissue, adjustment for these individual differences has only manipulated the total number of pulses the patient receives. However, titrating in the current domain, in accordance with embodiments of the invention, can be more efficient and require lower charge when determining the seizure threshold. Compared to traditional techniques, titration in the current domain may result in less severe cognitive side effects from the ECT treatment.

Two methods are generally used to determine if a seizure has been satisfactorily produced during the titration procedure. Most modern procedures use EEG signals to determine if a seizure has been produced. Typically, two channels of EEG monitors are connected to the patient to monitor for seizures. The second method is to monitor for motor seizures. This may be done using an optical motion sensor attached to the patient.

Once the titration procedure is completed and the seizure threshold is determined, the ECT system parameters are set to provide the desired treatment to the patient. Finally, the desired ECT signal is administered to the patient to induce seizures.

Figure 9:
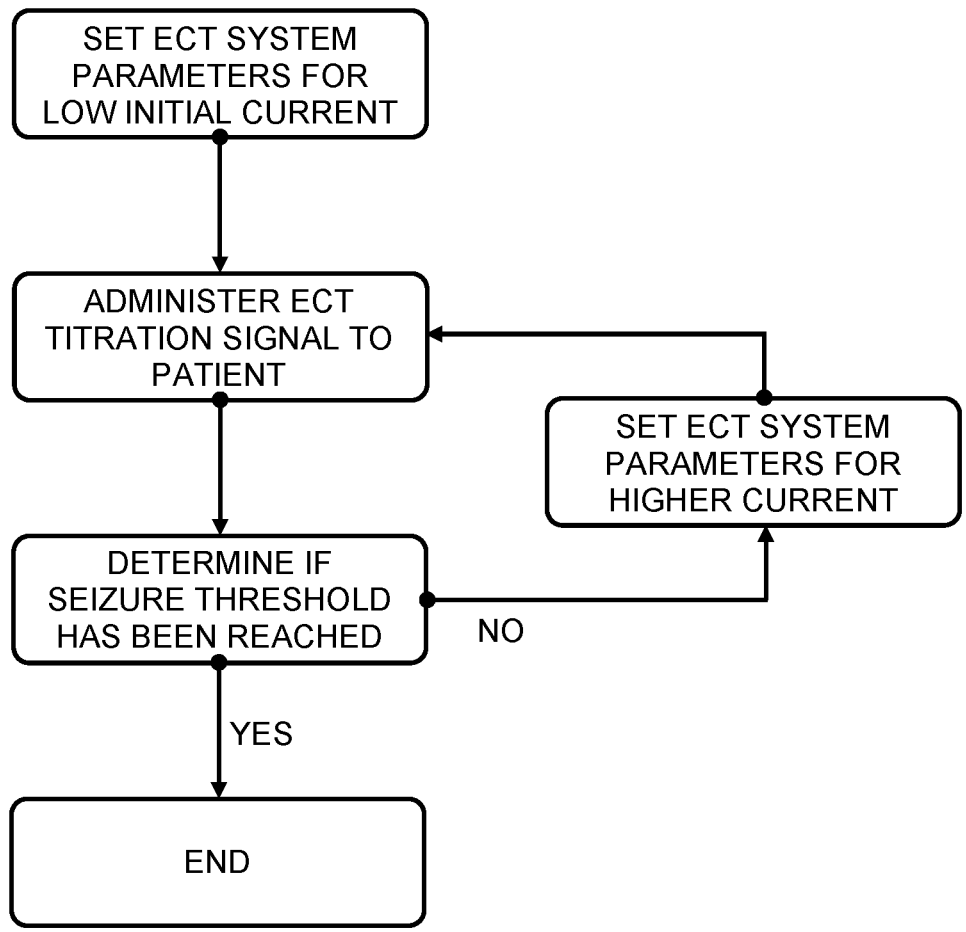
FIG. 9 is a flowchart of a method of titrating an ECT system in the current domain to determine a patient's seizure threshold.

FIG. 9 is a flowchart of a method of titrating an ECT system in the current domain to determine a patient's seizure threshold.

Referring to FIG. 9, the method of titrating an ECT system in the current domain includes first setting the parameters of the ECT system so as to provide a low current initial ECT signal to the patient. Conventional ECT systems have a minimum current level of 500 mA. However, according to some embodiments of the invention, a minimum current level of 100 mA may be used for titration in the current domain. Therefore, the low current initial ECT signal can be 100 mA. In the next step of the method, the low current initial ECT signal is administered to the patient. Then, a determination is made as to whether the patient's seizure threshold has been reached. If the seizure threshold is reached, the method ends. If the seizure threshold is not reached, the parameters of the ECT system are set to provide an incrementally higher current ECT signal, the higher current signal is administered to the patient, and a determination is made as to whether the patient's seizure threshold is reached. This process continues until the patient's seizure threshold is reached.

According to some embodiments of the invention, the current is doubled for each successive application of the stimulus until the seizure threshold is determined. Also, the current may be adjusted from about 100 mA to about 800 mA.

According to embodiments of the invention, the titration method can be performed by adjusting the current of the ECT signal rather than the number of pulses or the width of pulses as in conventional systems. Using the current titration method of the invention allows a more precise determination of the seizure threshold and thereby, minimizes adverse side effects of the treatment on the patient.

It should be appreciated that the above titration process may be embodied in an article of machine-readable media containing code that, when executed, causes the ECT system to perform these functions.

According to the invention, as described above, an ECT system includes a rectification circuit to allow unidirectional, or direct current stimulus to a patient. The ECT system also includes asymmetric positive and negative electrodes to allow focused stimulus of specific portions of the patient's brain.

According to some embodiments of the invention, a method of administering an ECT treatment to a patient includes adjusting the current of an ECT signal independently from the voltage to allow titration in the current domain. Therefore, a patient's seizure threshold can be more efficiently and reliably determined.

The foregoing is illustrative of the invention and is not to be construed as limiting thereof. Although a few example embodiments of the invention have been described, those skilled in the art will readily appreciate that many modifications are possible in the example embodiments without materially departing from the novel teachings and advantages of the invention. For example, several shapes and sizes of electrodes are specifically shown, but many more shapes and sizes of electrodes are possible. Accordingly, all such modifications are intended to be included within the scope of the invention as defined in the following claims.

What is claimed is:

1. A device for conducting electro-convulsive therapy (ECT), the device comprising:
   a signal generator configured to generate a seizure-inducing ECT stimulus, the ECT stimulus having a pulsed electric current component;
   a current controller configured to adjust an amplitude of the pulsed electric current component of the ECT stimulus to a constant current level between 100 milliamps and less than 500 milliamps; and
   at least two ECT stimulus electrodes configured to apply the ECT stimulus to a patient.

2. The device of claim 1, in which the current controller is adjustable by a user.

3. The device of claim 2, in which the adjustable current controller is adjustable through a user interface coupled to the current controller.

4. The device of claim 2 in which the adjustable current controller is configured to permit a user to set the adjustable current amplitude of the ECT stimulus above 500 milliamps and less than 800 milliamps.

5. The device of claim 2 in which the adjustable current controller is configured to permit a user to set the adjustable current amplitude of the ECT stimulus below 500 milliamps.

6. The device of claim 1, in which the ECT stimulus is bidirectional such that current pulses alternate in flow direction.

7. The device of claim 1, in which the ECT stimulus is unidirectional such that current pulses flow in a single direction.

8. The device of claim 1, in which the amplitude of the pulsed electric current component of the ECT stimulus is approximately 100 milliamps, and in which the current controller is structured to increase the amplitude of the pulsed electric current component of the ECT stimulus to a level above 100 milliamps.

\* \* \* \* \*